United States Patent [19]
Kalend et al.

[11] Patent Number: 5,727,554
[45] Date of Patent: Mar. 17, 1998

[54] APPARATUS RESPONSIVE TO MOVEMENT OF A PATIENT DURING TREATMENT/DIAGNOSIS

[75] Inventors: Andre M. Kalend, Monroeville; Joel Greenberger, Sewickley; Karun B. Shimoga, Pittsburgh; Charalambos N. Athanassiou, Pittsburgh; Takeo Kanade, Pittsburgh, all of Pa.

[73] Assignee: University of Pittsburgh of the Commonwealth System of Higher Education, Pittsburgh, Pa.

[21] Appl. No.: 715,834

[22] Filed: Sep. 19, 1996

[51] Int. Cl.$^6$ .................................................. A61B 6/00
[52] U.S. Cl. .................................................. 128/653.1
[58] Field of Search .................... 128/630, 653.1, 128/660.03; 364/413.02, 413.13, 413.25, 413.26; 356/375; 378/69, 205

[56] References Cited

U.S. PATENT DOCUMENTS

| | | | |
|---|---|---|---|
| 4,466,075 | 8/1984 | Groch et al. | 364/413.26 X |
| 5,080,100 | 1/1992 | Trotel | 128/653.1 |
| 5,103,823 | 4/1992 | Acharya et al. | 128/653.1 |
| 5,214,711 | 5/1993 | Neely et al. | 364/413.27 X |
| 5,295,483 | 3/1994 | Nowacki et al. | 128/660.03 |
| 5,389,101 | 2/1995 | Heilbrun et al. | 128/653.1 X |
| 5,398,684 | 3/1995 | Hardy | 128/653.1 |
| 5,446,548 | 8/1995 | Gerig et al. | 128/653.1 X |
| 5,482,042 | 1/1996 | Fujita | 128/653.1 |
| 5,558,430 | 9/1996 | Bova et al. | 128/653.1 |

OTHER PUBLICATIONS

Active Shape Models—'Smart Snakes', T.F. Cootes and C.J. Taylor, pp. 267–275, Proceedings of European Conference on Computer Vision, Genoa, Italy, 1992.

Training Models of Shape from Sets of Examples, T.F. Cootes, C.J. Taylor, D.H. Cooper, and J. Graham, pp. 8–18, Proceedings of European Conference on Computer Vision, Genoa, Italy, 1992.

A Computational Framework and an Algorithm for the Measurement of Visual Motion, P. Anandan, pp. 283–310, International Journal of Computer Vision, 2, 1989.

Feature Extraction from Faces Using Deformable Templates, A.L. Yuille, P.W. Hallinan, and D.S. Cohen, pp. 99–111, International Journal of Computer Vision, 8:2, 1992.

Computer and Robot Vision, vol. I, R. M. Haralick and L. G. Shapiro, pp. 328–353, Library of Congress Cataloging-in--Publication Data, 1992.

Motion Tracking with an Active Camera, D. Murray and A. Basu, pp. 449–459, IEEE Transactions on Pattern Analysis and Machine Intelligence, vol. 16, No. 5, May 1994.

*Primary Examiner*—Francis Jaworski
*Attorney, Agent, or Firm*—Richard V. Westerhoff; Eckert Seamans Cherin & Mellott, LLC

[57] ABSTRACT

A camera generates digital image signals representing an image of one or more natural or artificial fiducials on a patient positioned on treatment or diagnosis equipment. A processor applies multiple levels of filtering at multiple levels of resolution to repetitively determine successive fiducial positions. A warning signal is generated if movement exceeds certain limits but is still acceptable for treatment. Unacceptable displacement results in termination of the treatment beam. Tracking templates can be generated interactively from a display of the digital image signals or through automatic selection of an image having the median correlation to an initial template. A gating signal synchronized to patient breathing can be extracted from the digital image signals for controlling the radiation beam generator.

22 Claims, 12 Drawing Sheets

5,727,554

APPARATUS RESPONSIVE TO MOVEMENT OF A PATIENT DURING TREATMENT/DIAGNOSIS

BACKGROUND OF THE INVENTION

1. Field of the Invention

This invention relates to medical use of radiation for treatment and diagnosis, and more particularly to detection and response to patient movement during radiological treatment and diagnosis.

2. Background Information

Conventional radiotherapy treatment relies on simple patient setup techniques. These techniques use stationary and a limited number of radiation fields, which are often much wider than the tumor or volume, thus effectively compensating for the possibility of a tumor geometric miss. Consequently, a substantial amount of healthy tissue is irradiated and becomes a radio-biological dose limiting factor in tumor control.

Modern conformal dynamic radiotherapy attempts to overcome the above radio-biological limitation by tight-margin conformation of radiation dose distribution tailored to the three-dimensional tumor volume by the use of computer-control multibeam conformal dynamic radio therapy (CCRT). Consequently, the accuracy in patient position, knowledge of the movement of a patient including substantial motion of internal organs such as with breathing is of primary importance. In addition to patient movement which would cause the tight beam to miss the tumor, it is important to be able to detect patient movement which could cause a collision between the patient and the linear accelerator, which is repeatedly repositioned to establish the multiple treatment beams.

There is a need therefore for apparatus for detecting patient movement on radiological treatments/diagnostic equipment.

There is a particular need for such apparatus which can detect submillimeter patient movement in real time.

There is also a need for such apparatus which can detect patient movement initiated from various treatment positions.

There is also a need for such apparatus which can detect patient movement under varying lighting conditions.

There is a further need for such apparatus which can discriminate movement associated with patient breathing from other movement and accommodate therefor.

SUMMARY OF THE INVENTION

These needs and others are satisfied by the invention which is directed to apparatus responsive to movement of a patient which identifies and tracks movement of at least one passive fiducial on the patient. The apparatus applies multiple levels of filtering which can include: correlation, preferably normalized correlation, sparse sampling, bracketing and interpolation, and minima suppression to rapidly identify the location of the at least one fiducial. The multiple levels of filtering are applied at multiple levels of resolution of the digital image signals.

Interest operators can be used in combination with templates to locate the positions of the passive fiducials. The templates can be selected interactively by a user from a display generated by the digital image signals. Alternatively, the template used for tracking is selected from images generated using an initial template. Rather than using the image which best matches the initial template, the template with a median match is selected.

As another aspect of the invention, the means generating an output includes means indicating movement of the at least one passive fiducial relative to at least one selected level of displacement. Preferably, the output means generates a warning that movement exceeds a first displacement and includes means providing a signal for terminating radiation treatment when the movement exceeds a second greater displacement. Preferably, the means providing an indication of movement includes a display generating an image of the patient and the fiducials, together with an indication of movement relative to the first and second displacements.

As yet another aspect of the invention, the means determining movement of the passive fiducials includes means detecting movement associated with patient breathing and random movement. The movement associated with patient breathing can be used to generate a gating signal synchronized to patient breathing. This gating signal can then be used to actuate the beam generator only during selected parts of the breathing cycle.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENT

Figure 1:
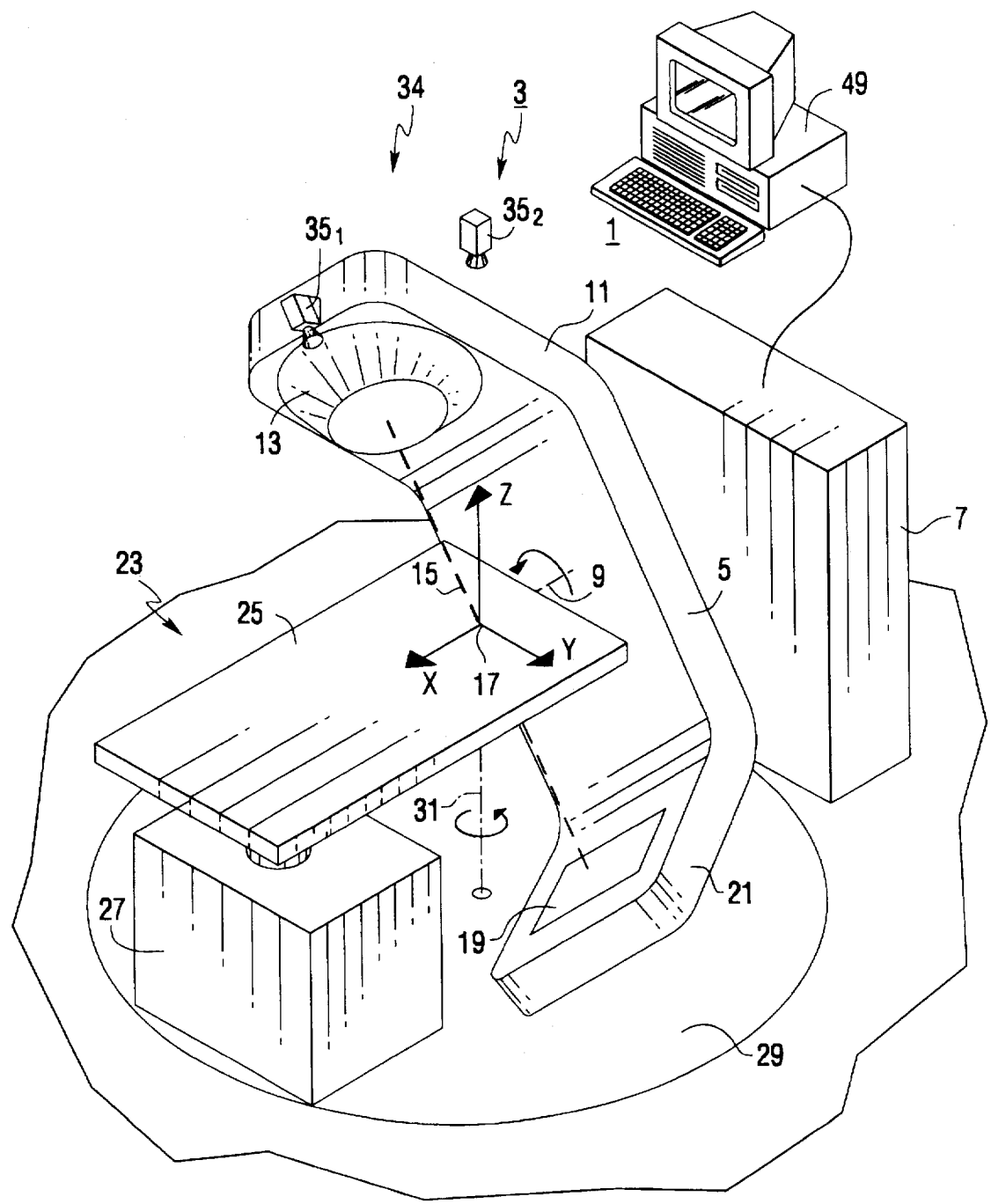
FIG. 1 is an isometric view of apparatus in accordance with the invention for implementing conformal dynamic radiotherapy.

FIG. 1 illustrates a radiotherapy treatment system 1 in which the invention is implemented. This system 1 includes a machine 3 having a gantry 5 pivotally mounted on a machine base 7 for rotation about a horizontal axis 9. The gantry 5 has a first arm 11 carrying a collimator 13 which directs a beam of high energy radiation 15, such as a beam of high energy photons, along a path which is perpendicular to and passes through an extension of the axis of rotation 9. This intersection is referred to as the isocenter 17. In some machines, a portal imager 19 is mounted on a second arm 21 on the opposite end of the gantry in alignment with the radiation beam 15. The portal imager 19 records radiation which is not absorbed by the patient.

The isocenter 17 serves as the origin of a coordinate system for room space. As can be seen, the X axis coincides with the axis of rotation 9 of the gantry. Thus, as the gantry 5 rotates it defines a plane of treatment containing the Y and Z axes.

The machine 3 further includes a patient positioning assembly 23, which includes a couch 25 mounted on a support 27 for vertical, lateral and longitudinal movement relative to the support. The support 27 is mounted on a turntable 29, which has its axis 31 vertically aligned under the isocenter 17 and concentric with the Z axis. With this arrangement, the patient positioning assembly 23 has four degrees of freedom: translation in the X, Y and Z axes of room space and rotation about the Z axis. Thus, the patient is not rotated about the longitudinal axis of the couch or tilted about a horizontal axis extending transversely through the couch. However, with the addition of rotation of the gantry in the Y-Z treatment plane, the radiation beam 15 can be directed through a patient reclining on the couch 25 in any desired direction. A computer 33 controls movement of the patient positioning assembly 23 and the gantry 5 for establishing the progression of high energy treatment beams used in practicing conformal radiation therapy.

As previously discussed, in conformal radiation therapy the beam 15 is tightly conformed by the collimator 13 to the specific tumor to be treated. Thus, movement of the patient on the couch 25 of the patient position assembly 23 can cause misalignment of the radiation beam 15 with the tumor. This not only degrades treatment of the tumor but also exposes surrounding healthy tissue to unwanted levels of radiation. In addition, normal breathing by the patient can cause movement of internal organs by an amount which would result in misalignment of the beam. For instance, a tumor on the lower portion of the lung can move several centimeters during normal breathing. Slight movement of the patient can be tolerated; however, treatment should be terminated if acceptable tolerances of movement are exceeded. Furthermore, excessive movement by the patient can also cause a collision between the patient and the gantry as the patient positioning assembly 23 and gantry are positioned for successive treatment beams.

Figure 2:
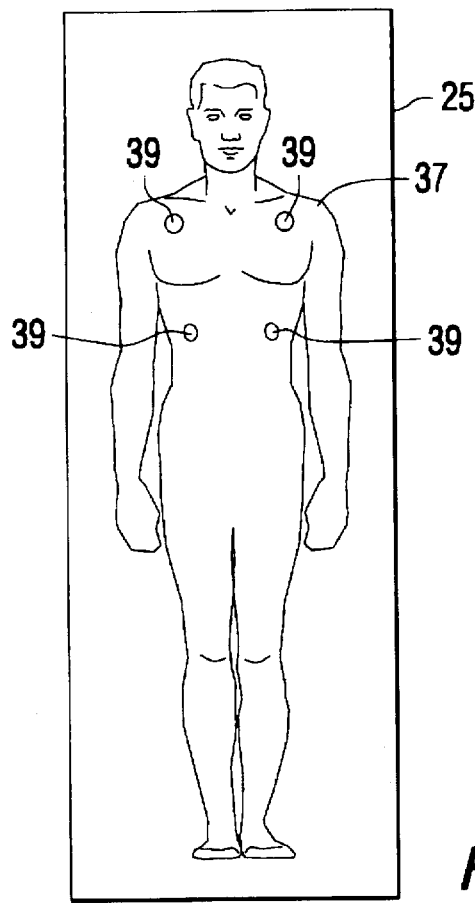
FIG. 2 is a plan view of a patient reclining on a couch which forms part of the apparatus of FIG. 1 and illustrating the placement of fiducials in accordance with the invention.

The invention employs a vision system 34 to measure and respond to patient movement. The vision system 34 includes at least one video camera 35. Preferably, multiple cameras are used. In the exemplary embodiment of the invention a first camera $35_1$ is mounted on the first arm 11 of the gantry 5 adjacent the collimator 13 and is aimed to capture an image of a patient 37 positioned on the couch 25, as shown in FIG. 2. As the camera $35_1$ will be below the couch 25 for some positions of the gantry 5, a second camera $35_2$ is fixed to the ceiling over the patient positioning assembly 23. The field of view of this camera $35_2$ will be blocked when the gantry 5 is at the top of its arc. Thus, the patient is visible to at least one camera 35 at all times. Additional cameras 35 could be provided, such as cameras laterally displaced from the patient positioning assembly 23 to provide more sensitivity to movement along the axis of, for instance, the camera $35_2$. However, as will be discussed below, a single camera can detect three-dimensional movement, including movement toward and away from the camera which is detected as a change in the size of the image.

Figure 3:
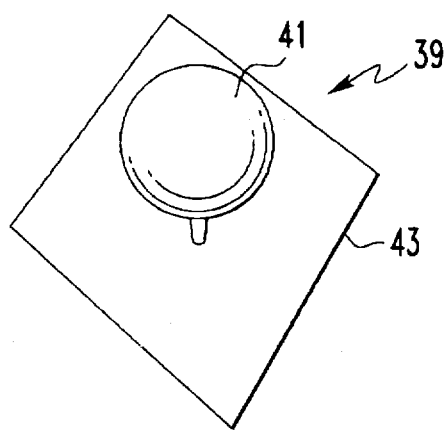
FIG. 3 is a perspective view of a preferred fiducial used in implementation of the invention.

In the exemplary embodiment of the invention, natural or artificial fiducials are used to detect patient movement. Natural fiducials could be scars or other prominent features of the patient. The preferred fiducial 39 shown in FIG. 3 is a sphere 41 covered with a material having a lambertian surface. Such a surface is highly reflective under low light conditions, yet provides a uniform scattered reflection with no highlights. The sphere 41 is attached to the center of a non-reflective base 43 which is secured to the patient's skin, such as by an adhesive.

In principle, only one fiducial 39 is required. As a practical matter, it is advantageous to provide multiple fiducials placed on the patient so as to detect any movement of the critical locations. Thus, as shown in FIG. 2, by way of example, four fiducials 39 are placed on the patient's chest. Natural skin markings could be used in addition to the artificial fiducials shown in FIG. 3. If more than one camera 35 is used, each tracks as many of the fiducials 39 as it can see.

Figure 4:
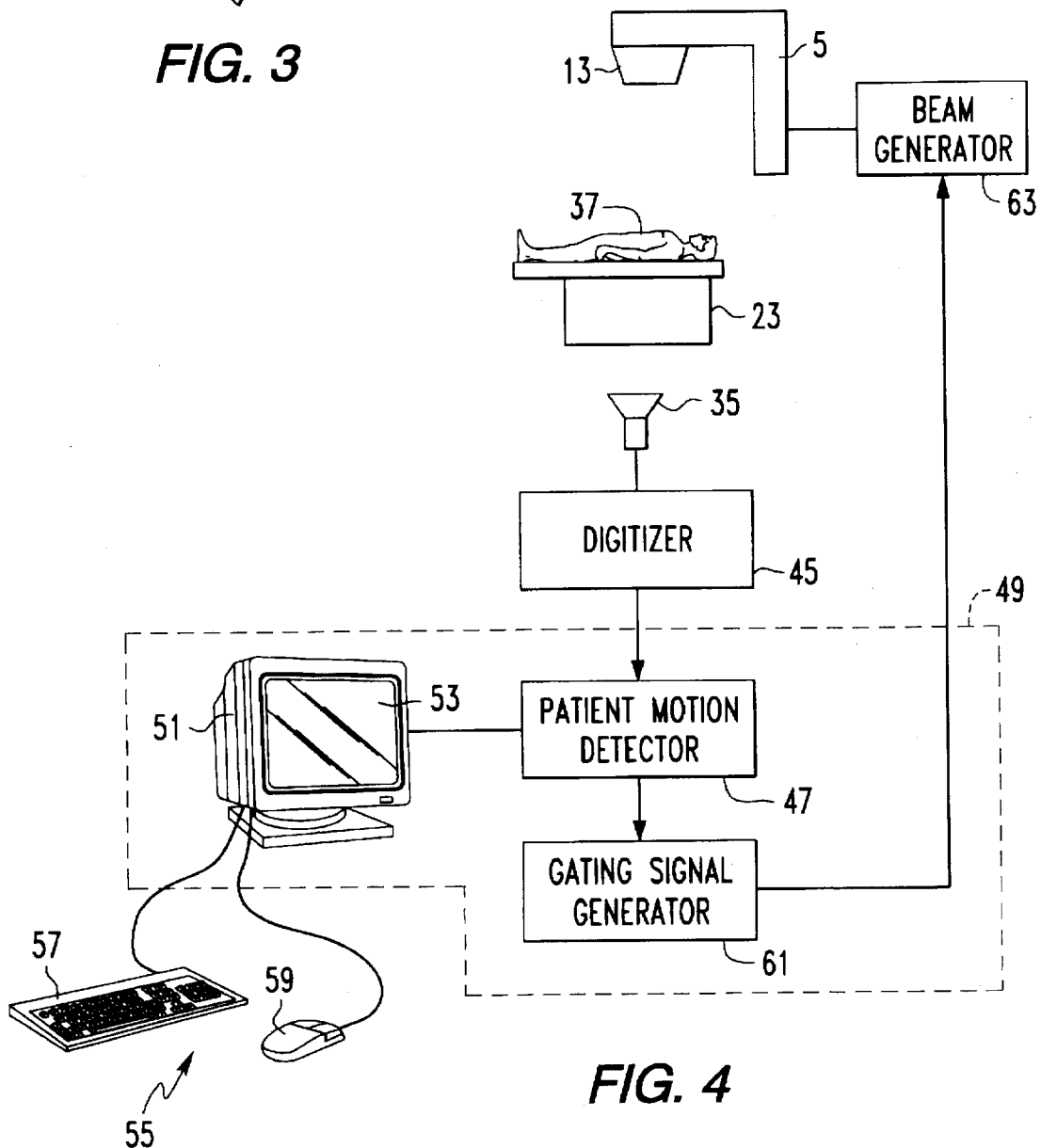
FIG. 4 is a functional diagram illustrating implementation of the invention.
Figure 5:
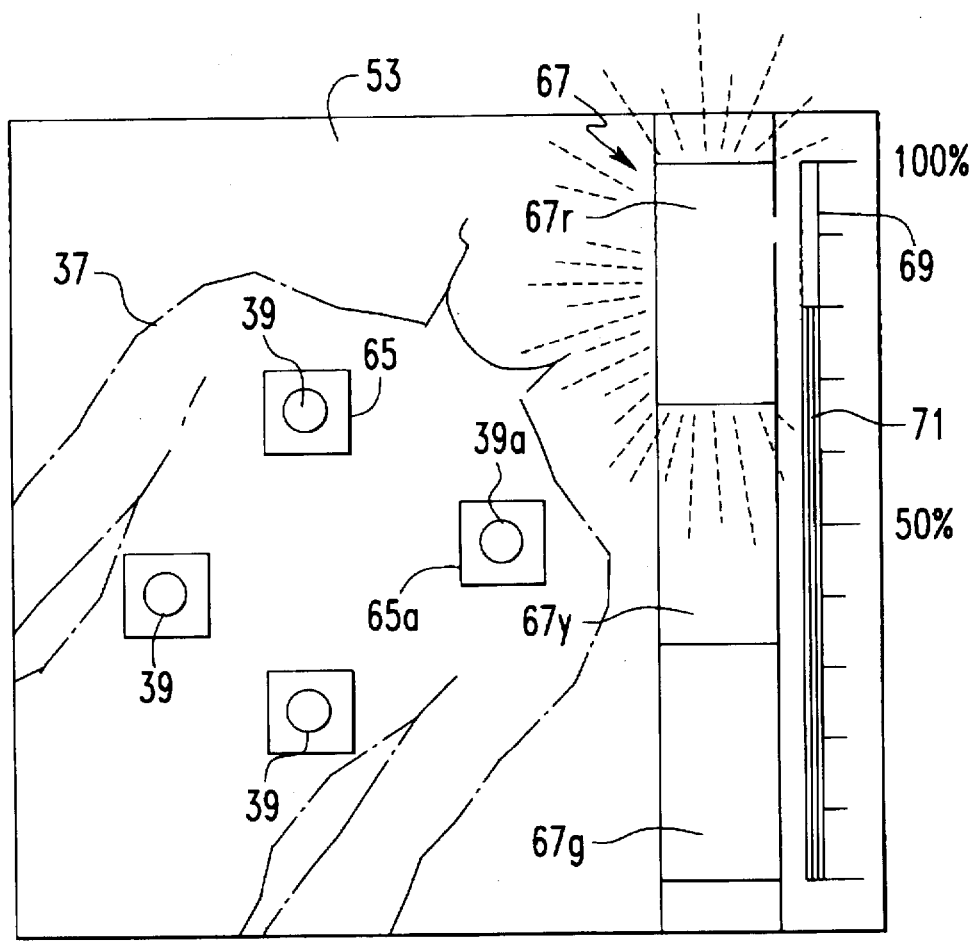
FIG. 5 is an illustration of a display which is generated by the apparatus of FIG. 1 in implementation of the invention.

FIG. 4 is a functional diagram of the invention. The camera(s) 35 capture an image of the fiducials 39 on the patient 37 reclining on the patient positioning assembly 23. The image captured by the camera 35 is digitized by digitizer 45 to generate digital image signals. These digital image signals are 0 to 255 gray scale signals for each camera pixel. The digital image signals are processed by a processor which includes a patient motion detector 47. Patient motion detector 47 is implemented in the computer 49 shown in FIG. 1. The computer 49 includes a monitor 51 which generates a display 53, an example of which is shown in FIG. 5. The man machine interface 55 for the computer 49 includes a keyboard 57 and a pointing device 59, such as a mouse or trackball.

As will be discussed fully, the patient motion detector 47 detects and identifies the fiducials 39 and then tracks their movement. Movement within a certain narrow tolerance is acceptable, while larger movements are unacceptable. Visible and/or audio warnings of these two classifications of movement can be generated. A gating signal generator 61 responds to unacceptable movement to disable the beam generator 63. This unacceptable movement which would terminate the radiation beam can be movement which displaces the target tumor so that it is missed by the radiation beam, or could be movement which would cause a collision between the patient and the gantry 5 during movement of the machine from one treatment beam to the next. In the former case, the gating signal generator 61 could re-enable the beam generator, if the patient returns to the proper position. For instance, a large sigh could temporarily displace the target area by an unacceptable amount. In accordance with another aspect of the invention, the patient motion detector 47 can track patient breathing and extract such quasi-periodic motion from random patient motion. Gating of the beam generator can then be synchronized with patient breathing. For instance, a tumor on the lung could move up to 4 to 5 centimeters during patient breathing. This is an unacceptable amount of movement. However, by synchronizing generation of the radiation beam with breathing, the tumor can be repetitively irradiated at a fixed position during the breathing cycle.

As shown in FIG. 5, the display 53 presents an image of the patient 37 with the fiducials 39 appearing prominently. An indicator 65, such as the square shown, surrounds each fiducial and is color coded to indicate the state of motion of the fiducial. The fiducial with the largest displacement such as 39a is singled out by a distinctive marker, such as a red square 65a, while the remaining markers are green squares in the exemplary system. The display also includes a traffic light 67 having a green section 67g, a yellow section 67y and a red section 67r. When motion of the fiducials is within preferred tolerances, the green section 67g of the traffic light is on. For motion which is outside the normal range, but which is still acceptable, the yellow section 67y is on. The traffic light turns red when the motion of any of the fiducials is approaching the unacceptable. A scale 69 along the side of the display 53 indicates in bar graph form the percentage of maximum allowable displacement of the fiducial of maximum displacement. Thus, for instance, if the red light 67r is illuminated and the bar graph 71 indicates 80%, the fiducial with maximum displacement has moved by a distance which is four fifths of the way through the acceptable displacement. The green, yellow and red regions need not be equal as shown in the example.

Detection of motion of a patient using passive fiducials requires an implementation which is robust enough to accommodate for the variations in the shapes, appearance and lighting conditions to which the fiducials are subjected and, at the same time, is fast enough to provide real time tracking of patient movement. The invention satisfies these requirements by utilization of successive levels of filtering and templates which are modified to accommodate for actual conditions. The result is a system which can track patient movement at 20 Hz or better.

Figure 6:
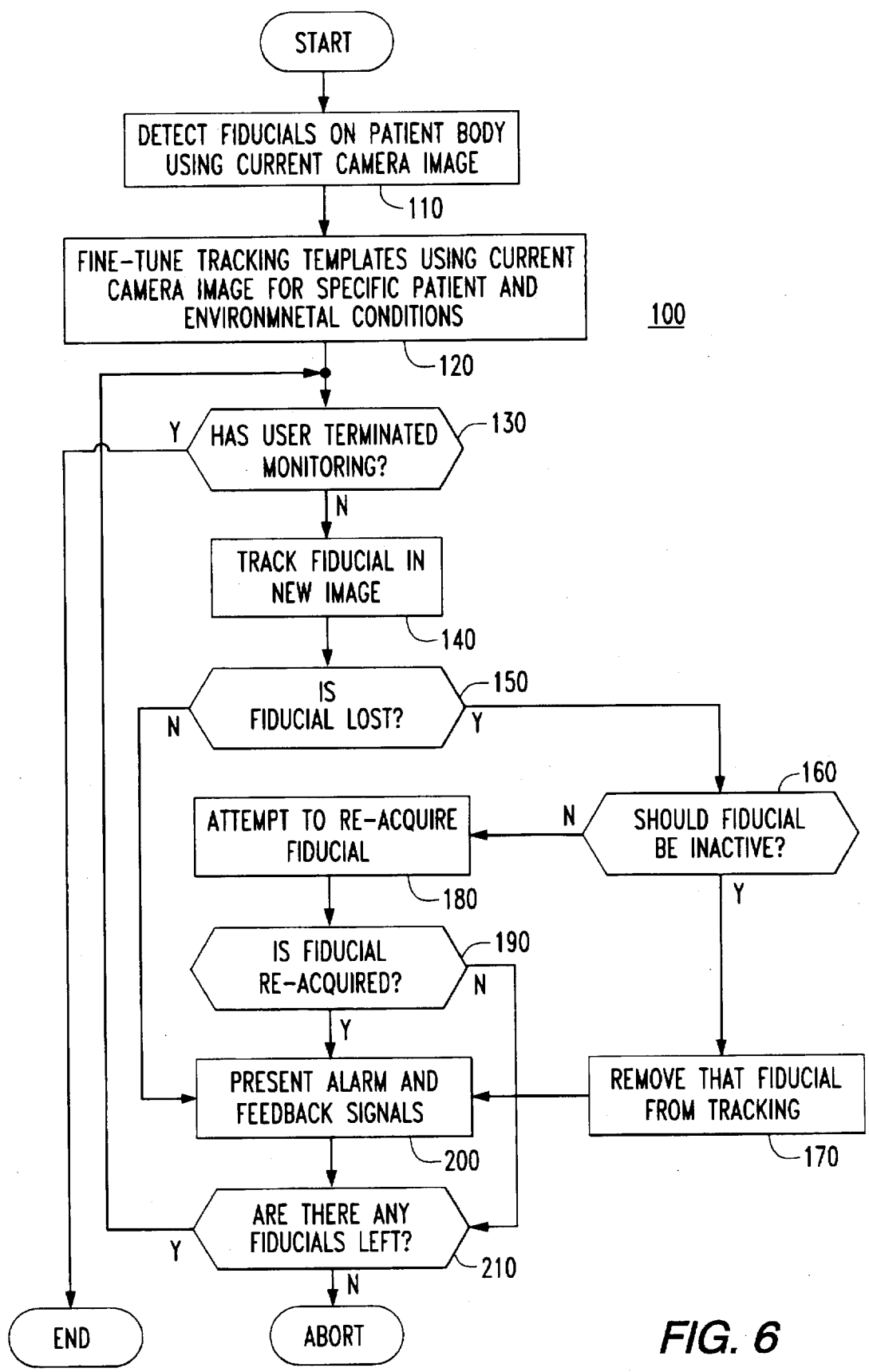

Flow charts of suitable software 100 for implementing the invention are illustrated in FIGS. 6–16. FIG. 6 illustrates the main routine of the software 100 and includes detecting fiducials on the patient's body is in the current camera image at 110. As will be described, this is accomplished utilizing templates. The templates are then fine tuned at 120 for the specific patient and environmental conditions. As long as the user desires monitoring as determined at 130, a loop is entered in which each individual fiducial is tracked as indicated at 140. It is possible that a fiducial can be lost by the tracking system. This could occur, for instance, if the patient moves so that a fiducial is blocked from the camera's view, or the patient moves a hand through the line of sight of the camera. Also, a fiducial may be temporarily lost by rapid movement or adverse lighting conditions. If a fiducial is lost, as determined at 150, a number of attempts can be made to reacquire it. If the fiducial is not reacquired within a reasonable time, however, it is removed from tracking as indicated by 160 and 170. If the selected number of attempts to reacquire, such as for example, five, have not been reached, an attempt is made to reacquire the fiducial at 180. If the fiducial is reacquired at 190, then a routine is run at 200 to generate any alarm if needed, and gating signals for the accelerator or beam generator 63 as indicated at 200. As long as any fiducials remain to be tracked as indicated at 210, the tracking loop is repetitively run.

Figure 7:
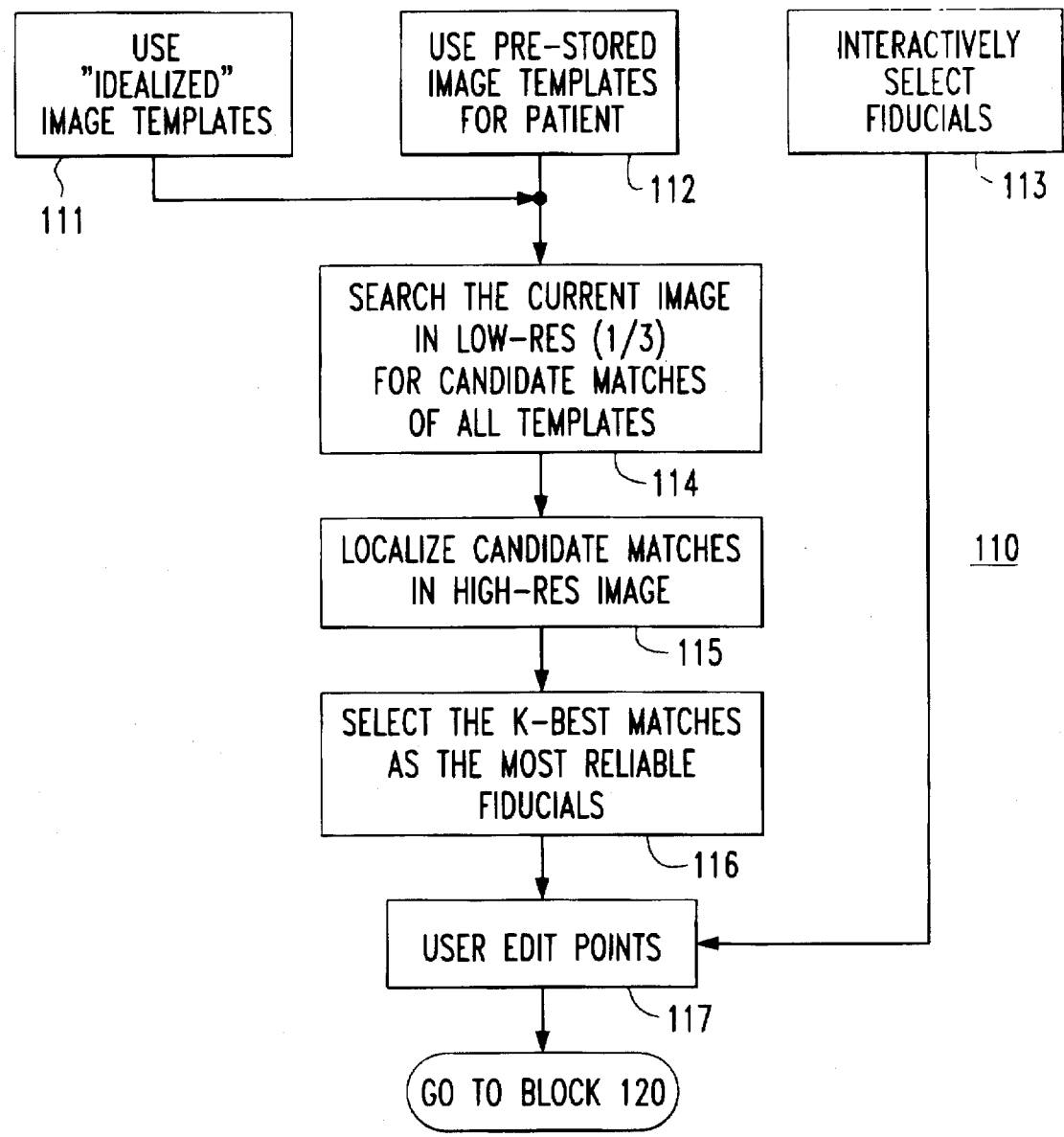

FIG. 7 illustrates the general routine 110 for detecting the fiducials 39 in the image represented by the digital image signals. As mentioned, templates are used to identify the locations of the fiducials. The templates indicate what the pattern of digital signals representing the fiducial should look like. The size of the templates used must be considered. Larger templates improve the accuracy but take longer to process. In the exemplary system, templates 40 pixels square have been utilized. There are several ways in which the templates can be generated. As indicated at 111 in FIG. 7, idealized image templates can be utilized. In addition to such idealized templates or in place thereof, pre-stored image templates for the patient can be used as indicated at 112. Such pre-stored templates are used, for instance, for natural fiducials such as scars. One template is used for each family of fiducials. For instance, if all of the fiducials are the preferred fiducials such as shown in FIG. 3, only one template is required because all of the fiducials in the family will generate a similar image.

In addition, templates can be selected interactively by the user at 113. This is accomplished by using the mouse or trackball 59 to click on the center of a representation of the fiducial on the display 53.

Where the idealized or pre-stored templates are utilized, a multiresolution pyramid is used to locate the fiducials in the image using the templates. Thus, as indicated at 114, a search is made of the current image in low resolution for candidate matches of all template families. In the exemplary embodiment of the invention, one-third resolution is used at this point. Matches are made using a normalized correlation between the template and the image. The matches found in low resolution are then verified and localized in high resolution at 115. The K best matches are then selected as the most reliable fiducials at 116 where K equals the number of fiducials to be tracked. The user is then given the opportunity at 117 to edit the detected location of fiducials found either through use of the idealized or pre-stored templates or templates generated interactively.

Figure 17:
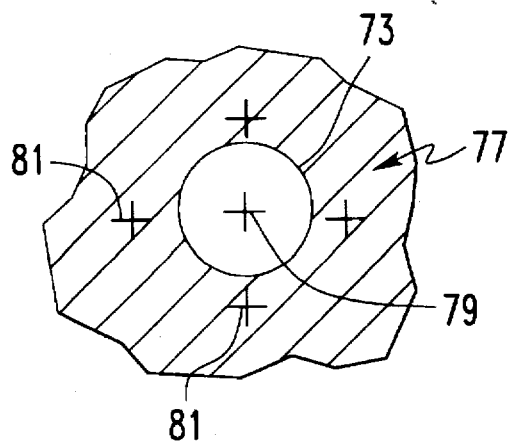
FIG. 17 is an illustration of an interest operator which can be used in implementation of the invention.
Figure 8:
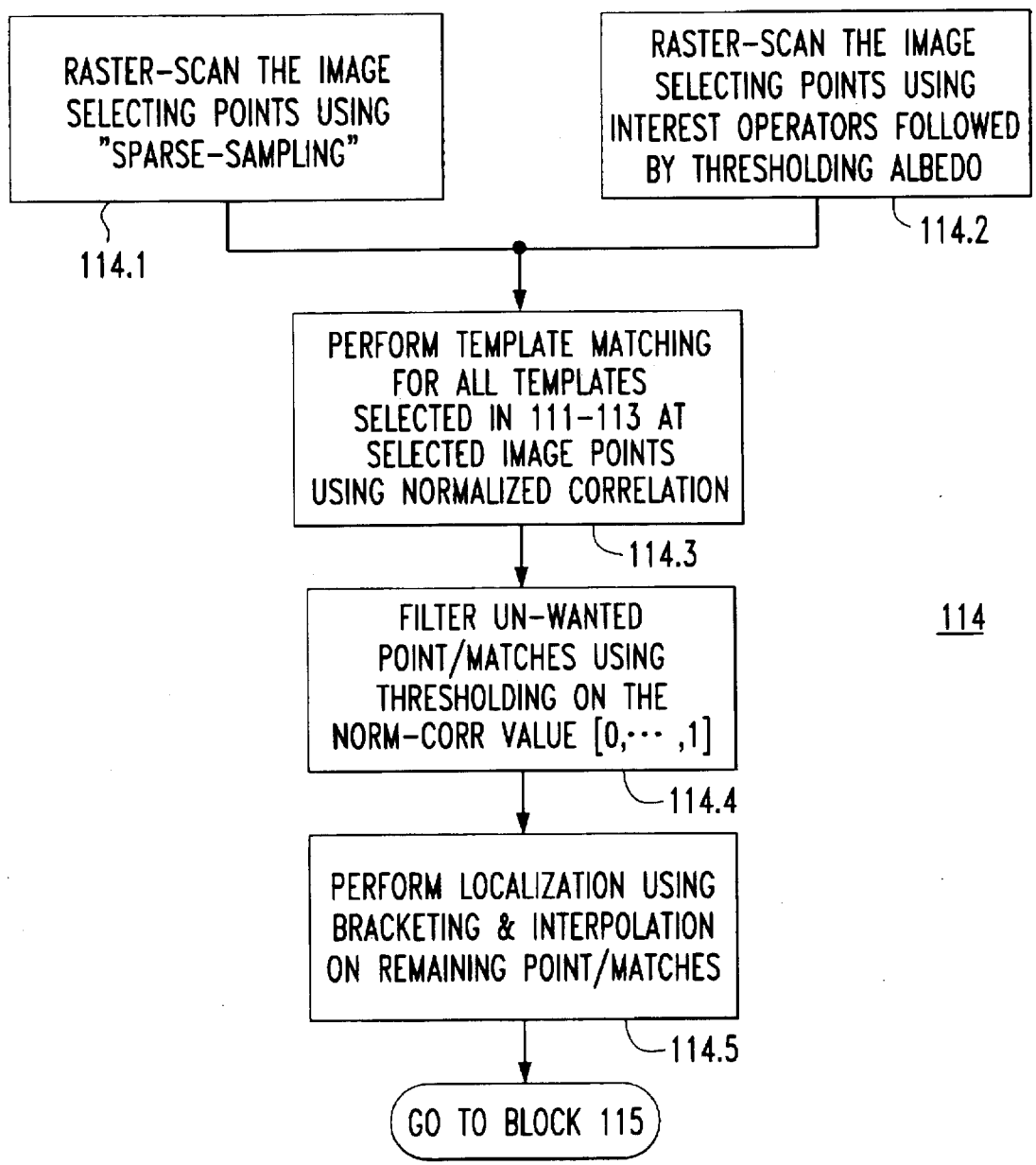

The details of the low resolution detection routine performed in block 114 of FIG. 7 is shown in FIG. 8. As shown at 114.1, the image can be raster scanned selecting points using sparse sampling. In raster scanning pixels are considered successively along each line, line-by-line in increments of one, while in sparse sampling the increment is greater than one. Alternatively, the image can be raster scanned as indicated at 114.2, selecting candidate points using interest operators followed by thresholding. Interest operators are simple patterns which emphasize gray scale characteristics of a particular fiducial. An example is shown in FIG. 17, where the fiducial is a light circle 73 on a dark background 75. The interest operator 77 could be, for instance, the one pixel value 79 in the center having a gray scale value matching that of the light circle 73, and the four pixels 81 at the cardinal points having gray scale values similar to that of the background 75. Such interest operators permit rapid searching of the image and should be selected as to assure identifying all of the fiducials in the family. They will most likely also generate additional candidate points. Returning to FIG. 8, the interest operator generated value in the exemplary system is the relative albedo. The relative albedo of each point in the low resolution scan is compared to a threshold value to select candidate points.

For each candidate point, a template matching is performed at 114.3, using a normalized correlation. Unwanted point matches are then filtered out at 114.4 using thresholding on the normalized correlation value. In the exemplary embodiment, a normalized correlation of 0.75 was used as the threshold. Bracketing and interpolation are then used at 114.5 to localize the remaining point/matches. In implementing bracketing, a rectangular image window is selected within which the desired point match will definitely lie. Then by interpolating between the correlation values of points on the border of the selected window along with its center, a new estimate of the location of the point match is calculated. This process is repeated with successively smaller windows centered on the new estimate of the location of the point match until a singular point is reached. In the exemplary system, the interpolation is performed using a two-dimensional Gaussian distribution.

Figure 9:
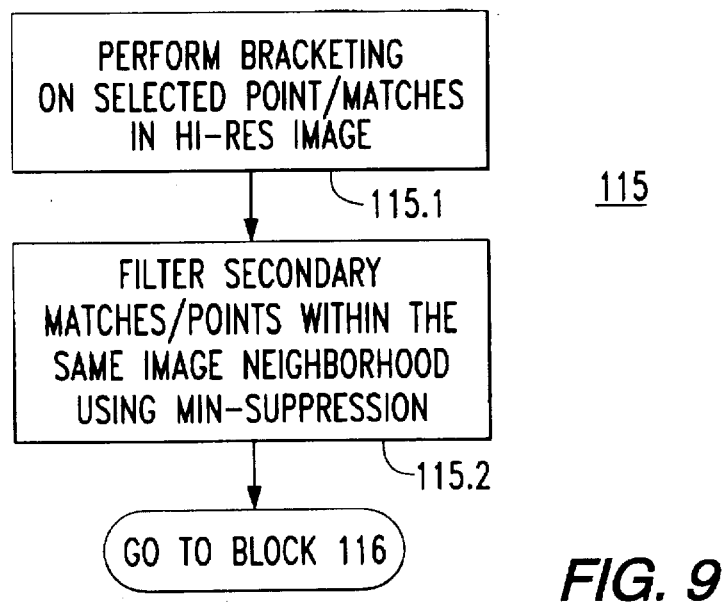
FIGS. 6–16 are flow charts of software used in implementation of the invention.

FIG. 9 illustrates the techniques for verifying the candidate matches in high-resolution indicated at 115 in FIG. 7. Bracketing is performed on the selected matches in high resolution as indicated at 115.1. These points are then filtered at 115.2 within the same image neighborhood using minima suppression. In implementing minima suppression, for each point which has been a match, an area the size of the template is centered on the point. A point is selected as a further candidate match only if it is the best correlation with the template within the template window.

Figure 10:
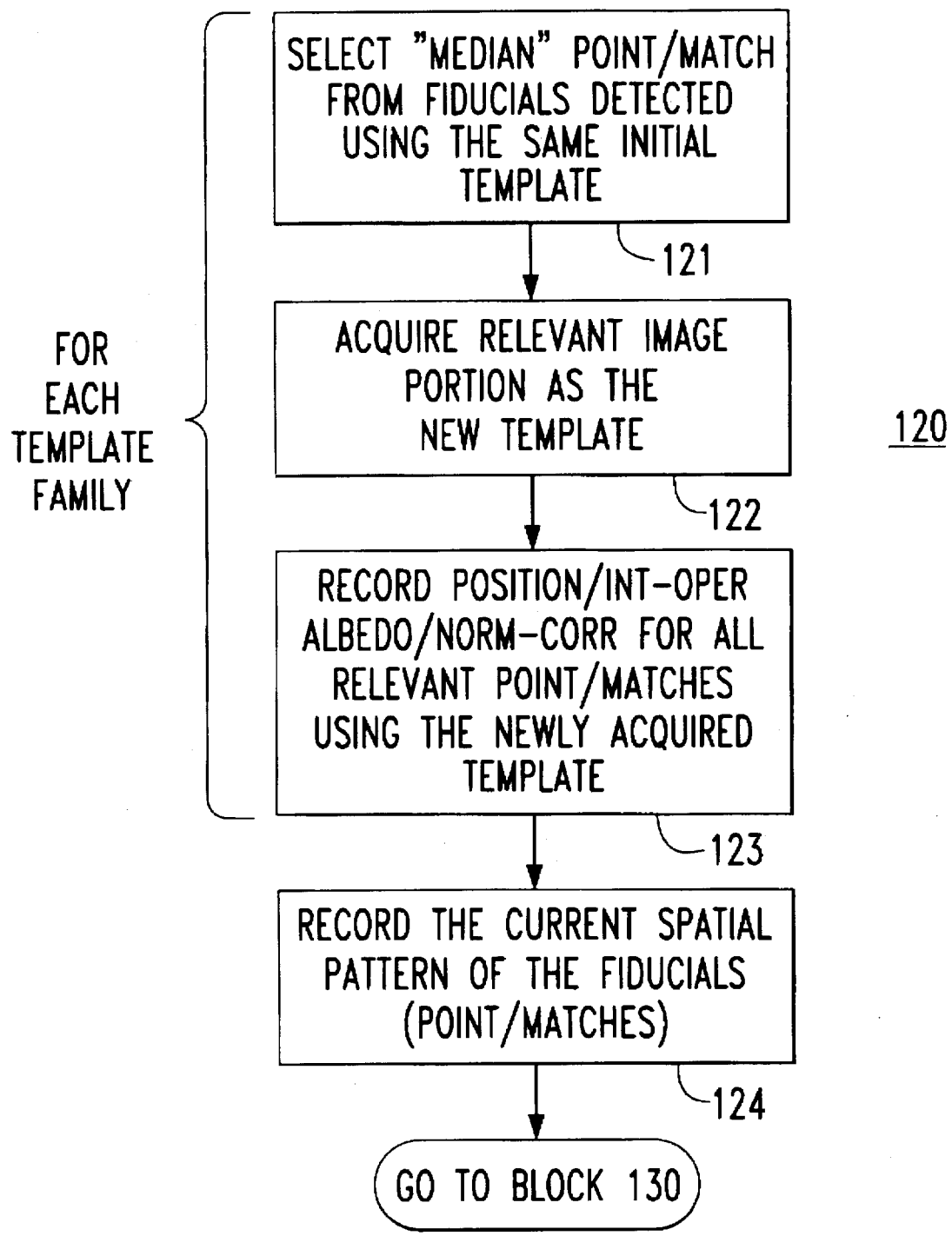

An important aspect of the invention is the fine tuning of the tracking templates called for at 120 in FIG. 6. FIG. 10 illustrates the details of fine tuning the templates. As indicated at 121, the median point/match from fiducials detected using the same initial template is selected. For example, if there are three point matches for a fiducial family, the match having the middle value of correlation is selected. Notice that the match with the best correlation is not selected as it is likely to eliminate some valid matches. This technique adapts the selection of the template to be used for tracking to the actual conditions existing at the time of the selection. The relevant image portion is then acquired as the new template at 122, and the position, the interest operator value and the normalized correlation for all relevant point/matches using this newly acquired template is then recorded at 123. The steps 121–123 are accomplished for each template family. Then, the current special pattern of all the fiducials determined by the point/matches, is recorded at 124.

Figure 11:
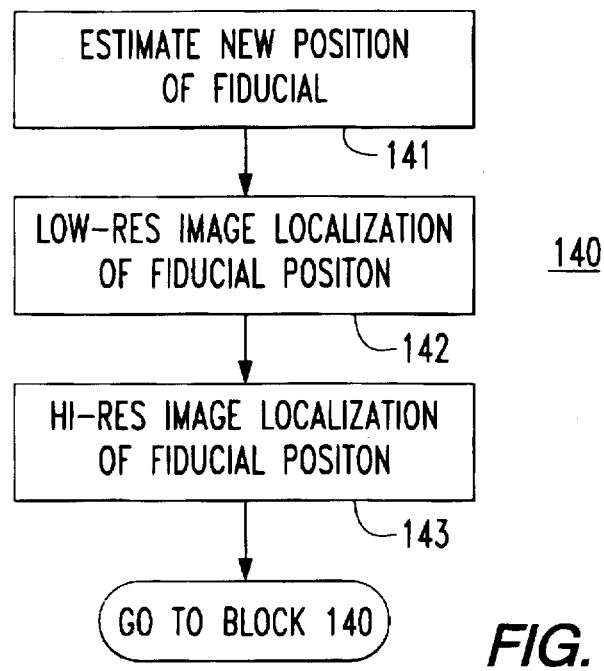

The program then enters the tracking loop at block 130 in FIG. 6. The routine for continuous tracking, which is called at 140 in FIG. 6 is illustrated in FIG. 11. The new position of the fiducial is estimated at 131 by projecting a velocity vector calculated from prior positions of the fiducial. Localization of fiducial position is then implemented in low resolution using bracketing and interpolation as indicated at 132. This is followed by high resolution localization of the fiducial position at 133, also using bracketing and interpolation.

Figure 12:
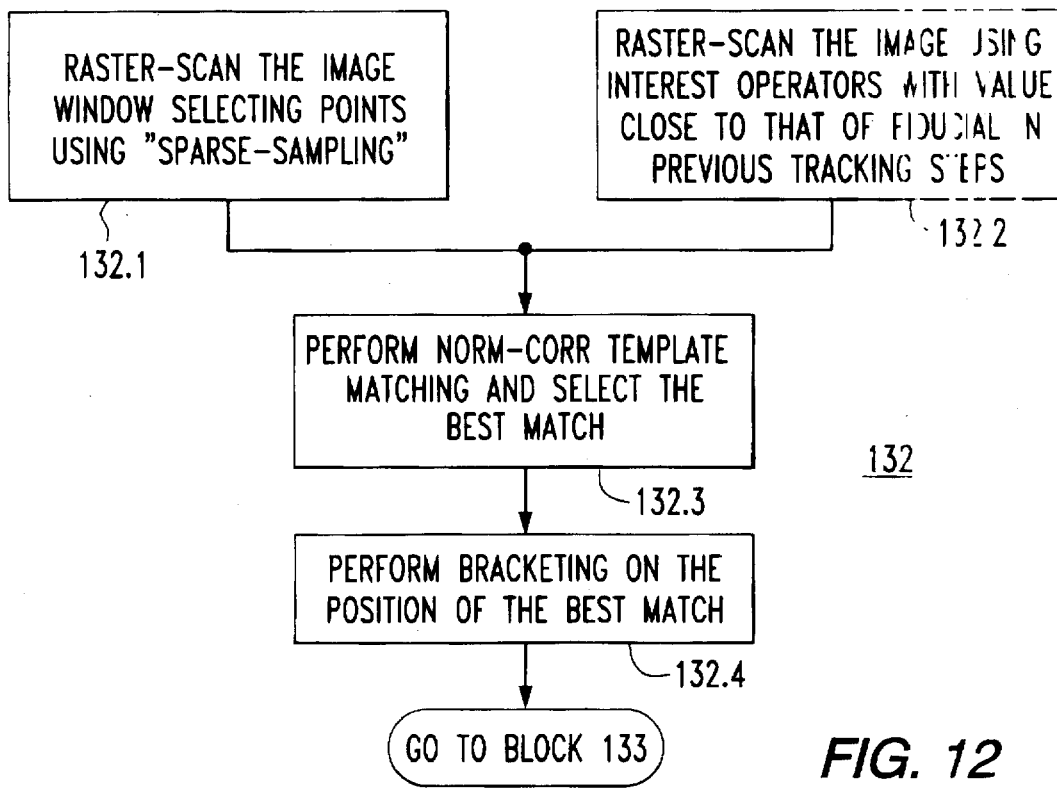

The low resolution localization of block 131 is implemented by the routine illustrated in FIG. 12. As indicated at 132.1 points are selected by raster scanning the image window using sparse sampling. If interest operators are used, the interest operators with the value closest to that of the fiducial in the previous tracking step is selected at 132.2. In either case, a best match is selected using normalized correlation template matching at 132.3. This is followed by bracketing on the position of the best match at 132.4.

Figure 13:
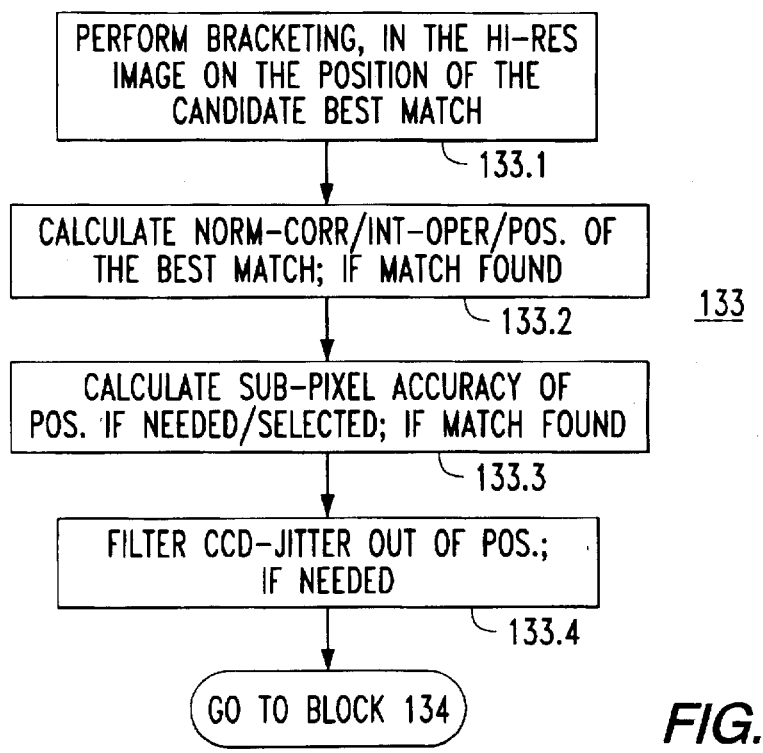

FIG. 13 illustrates the high resolution localization of fiducials called for in block 133 of FIG. 11. As indicated, bracketing is performed on a candidate with best match in high resolution as indicated at 133.1. If a match is found, the normalized correlation, interest operator value and position of the best match are calculated at 133.2. If desired, the sub-pixel accuracy of the position can be calculated at 133.3. The same interpolation technique as in bracketing and interpolation, as described above, is used. Alternatively, bilinear interpolation between the surrounding pixel correlation values could be used. Finally, if needed, charge coupled device (CCD) jitter is filtered out of the position at 133.4. In the exemplary system, a low pass filter is used.

Figure 14:
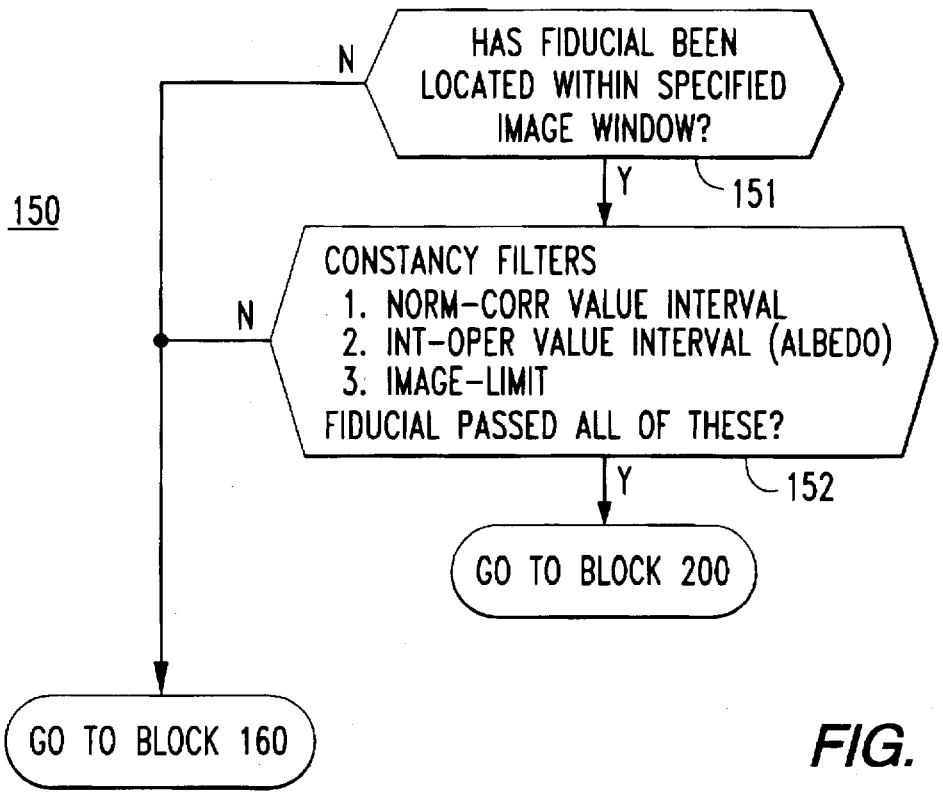

The lost fiducial routine 150 in FIG. 6 is shown in FIG. 14. If the tracking routine finds no fiducial within the specified image window at 151, then clearly the fiducial has been lost. Even if a fiducial has been found, confirmation must be made that it is in fact the new position of the fiducial. Hence, a number of constancy tests are applied in 152. For instance, the normalized correlation value and the interest operator value must not change by more than a selected amount, such as, for example, 15%, from the most current values. Also, image limits are applied. For instance, the fiducial should not have changed position by more than a predetermined amount or, if the edge of the image is reached, the position indicated is not accepted as the fiducial may be out of the field of view, although a continued indication that it is at the edge may be presented.

Figure 15:
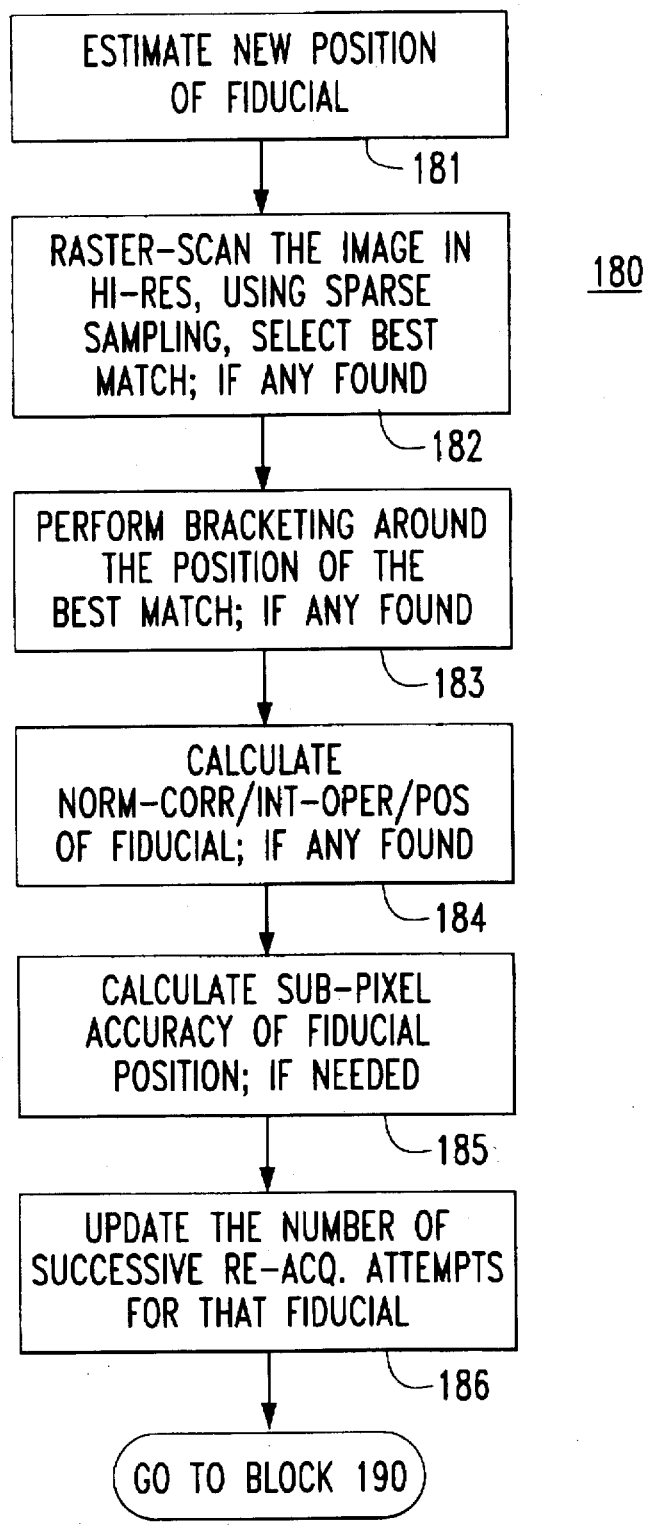

The routine 180 in FIG. 6 for reacquiring the lost fiducial is shown in FIG. 15. First, the new position of the fiducial is estimated at 181 using a larger search window than was used at 141 in FIG. 11. The image window is then raster scanned in high resolution using sparse sampling to select the best match, if any, at 182. Bracketing is then performed around the position of the best match, if any, at 183. The normalized correlation interest operator albedo and the position of the fiducial best matched is then determined at 184. This is followed by calculation of sub-pixel accuracy, if needed, at 185. Finally, the number of successive attempts to reacquire the fiducial is updated at 186.

Figure 16:
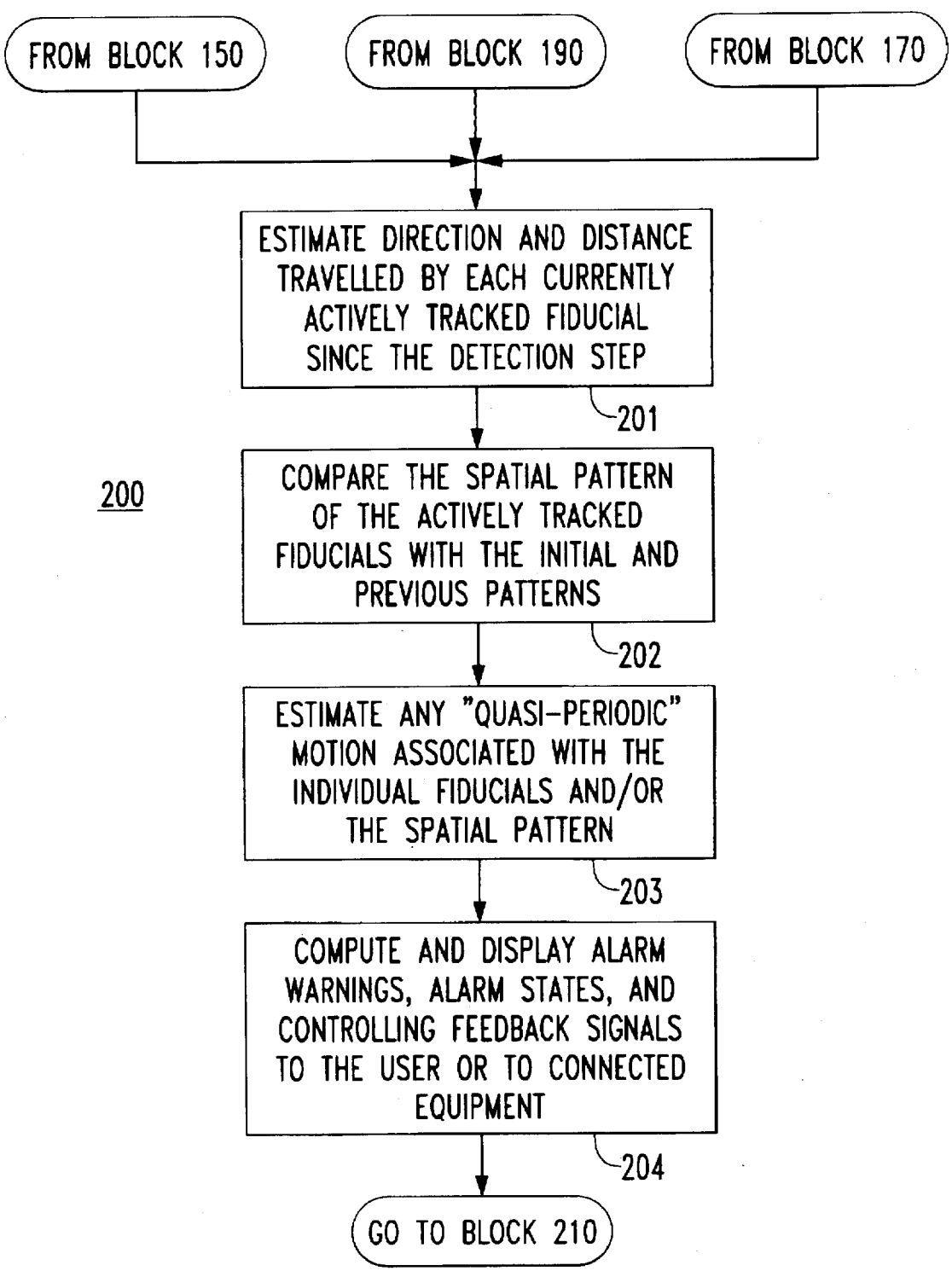

FIG. 16 illustrates the routine 200 in FIG. 6 for generating the alarms and gating the accelerator or beam generator. The direction and distance traveled by each currently actively tracked fiducial since the detection step is estimated at 201. The special pattern of the actively tracked fiducials is compared with the initial pattern and previous patterns at 202. Any quasi-periodic motion associated with the individual fiducials and/or the special pattern is predicted at 203 such as by using past data analysis. This would include movement associated with breathing or tremor of the patient. The alarm warnings, alarm states and accelerator gating signals are then computed at 204 for display or for feedback to the equipment, such as the accelerator.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

What is claimed is:

1. Apparatus responsive to movement of a patient positioned on a patient positioning assembly during treatment/diagnosis, said apparatus comprising:

camera means generating digital image signals representing an image of at least one passive fiducial having a lambertian surface on said patient; and processing means comprising means responsive to actual shape, appearance and lighting conditions of said at least one passive fiducial having a lambertian surface in said image represented by said digital image signals to determine successive positions of said at least one passive fiducial having a lambertian surface, means repetitively determining movement of said at least one passive fiducial having a lambertian surface from said successive positions, and means generating an output in response to predetermined values of said movement.

2. Apparatus responsive to movement of a patient positioned on a patient positioning assembly during treatment/diagnosis, said apparatus comprising:

a single camera generating digital image signals representing an image of at least one fiducial on said patient; and processing means comprising means responsive to actual shape, appearance and lighting conditions of said at least one fiducial in said image represented by said digital image signals to determine successive positions of said at least one fiducial, means tracking three-dimensional movement of said at least one fiducial from said successive positions and means generating an output in response to predetermined values of said movement.

3. The apparatus of claim 2, wherein said means repetitively determining movement of said at least one fiducial includes means detecting movement associated with patient breathing, and said output means comprises means generating a gating signal synchronized to said patient breathing.

4. The apparatus of claim 2, wherein said processing means comprises means repetitively applying multiple levels of filtering to said digital image signals to determine successive positions of said at least one fiducial.

5. The apparatus of claim 4, wherein said means applying multiple levels of filtering includes means applying bracketing and interpolation to said digital image signals to determine position of said at least one fiducial.

6. The apparatus of claim 4, wherein said means applying multiple levels of filtering includes means applying minima suppression to said digital image signals.

7. The apparatus of claim 4, wherein said means applying multiple levels of filtering include means applying at least two types of filtering selected from a group consisting of correlation, sparse sampling, bracketing and interpolation, and minima suppression.

8. The apparatus of claim 7, wherein said processing means includes means using multiple levels of resolution of said digital image signals to determine successive positions of at least one fiducial and said means applying multiple levels of filtering comprise means applying filtering at each of said multiple levels of resolution.

9. The apparatus of claim 4, wherein said processing means includes means using at least one of templates and interest operators to determine successive positions of said at least one fiducial from said digital image signals.

10. The apparatus of claim 2, wherein said pressing means comprises means using a template to successively determine position of said at least one fiducial and means selecting said template.

11. The apparatus of claim 10, wherein said at least one fiducial comprises a plurality of fiducials, and said means selecting a template includes means generating an initial template, means generating template matches for each of said plurality of fiducials from said digital image signals using said initial template, and means selecting one of said template matches for use in determining positions of each of said plurality of fiducials.

12. The apparatus of claim 11, wherein said means selecting said one of said template matches includes means generating a value for each of said templates matches, and means selecting a template match having a median value as said one template match.

13. Apparatus responsive to movement of a patient positioned on a patient positioning assembly during treatment/diagnosis, said apparatus comprising:

camera means generating digital image signals representing an image of at least one fiducial on said patient; and processing means comprising means responsive to actual shape, appearance and lighting conditions of said at least one fiducial in said image represented by said digital image signals to determine successive positions of said at least one fiducial at a rate of at least 20 Hz, means tracking movement of said at least one fiducial from said successive positions, and means generating an output in response to predetermined values of said movement.

14. The apparatus of claim 13, wherein said means generating an output includes means generating an indication of movement relative to at least one selected level of displacement.

15. The apparatus of claim 14, wherein said means generating said indication of movement indludes means providing a warning that said movement exceeds a first displacement and means providing a signal for terminating radiation treatment/diagnosis when said movement exceeds a second displacement greater than said first displacement.

16. The apparatus of claim 14, wherein said means generating an indication of movement comprises display means generating an image of said fiducials and an indication of said movement relative to said first and second displacements.

17. The apparatus of claim 16, wherein said camera means includes means generating digital image signals for a plurality of fiducials, said means repetitively determining movement determines movement of each of said plurality of fiducials, and said display means includes indicator means indicating a fiducial with the greatest movement.

18. The apparatus of claim 14, wherein said means repetitively determining movement includes means detecting movement associated with patient breathing and random movement, and wherein said means generating an indication of movement indicates said random movement.

19. Apparatus responsive to movement of a patient positioned on a patient positioning assembly during treatment/diagnosis, said apparatus comprising:

camera means generating digital image signals representing an image of at least one fiducial on said patient; and processing means comprising means responsive to actual shape, appearance and lighting conditions of said at least one fiducial in said image represented by said digital image signals to determine successive positions of said at least one fiducial, means repetitively determining movement of said at least one fiducial from said successive positions, and means generating an output in response to predetermined values of said movement;

said processing means further comprising means using a template to successively determine position of said at least one fiducial and means selecting said template comprising display means, means generating on said display means an image of said at least one fiducial from said digital image signals and user interface means for selection of a template from said image of said at least one fiducial.

20. Apparatus responsive to movement of a patient positioned on a patient positioning assembly, said apparatus comprising:

camera means generating digital image signals representative of an image of said patient; and processing means comprising means determining movement of said patient from said digital image signals, including movement associated with breathing by said patient, and gating means generating gating signals synchronized with said movement associated with breathing by said patient.

21. The apparatus of claim 20, wherein said camera means generates said digital image signals representing an image of at least one fiducial on said patient, and said means determining movement of said patient includes means determining movement of said at least one fiducial.

22. The apparatus of claim 20 adapted for use during treatment of said patient with a radiation beam generated by a beam generator, wherein said gating means comprises means generating said gating signals synchronized to actuate said beam generator in synchronism with patient breathing.

* * * * *

US005727554C1

(12) EX PARTE REEXAMINATION CERTIFICATE (7563rd)
United States Patent
Kalend et al.

(10) Number: US 5,727,554 C1
(45) Certificate Issued: Jun. 22, 2010

(54) APPARATUS RESPONSIVE TO MOVEMENT OF A PATIENT DURING TREATMENT/DIAGNOSIS

(75) Inventors: Andre M. Kalend, Monroeville, PA (US); Joel Greenberger, Sewickley, PA (US); Karun B. Shimoga, Pittsburgh, PA (US); Charalambos N. Athanassiou, Pittsburgh, PA (US); Takeo Kanade, Pittsburgh, PA (US)

(73) Assignee: University of Pittsburgh of the Commonwealth System of Education, Pittsburgh, PA (US)

Reexamination Request:
No. 90/009,534, Aug. 25, 2009

Reexamination Certificate for:
Patent No.: 5,727,554
Issued: Mar. 17, 1998
Appl. No.: 08/715,834
Filed: Sep. 19, 1996

(51) Int. Cl.
*A61B 6/00* (2006.01)
*A61B 6/04* (2006.01)

(52) U.S. Cl. .......................................... 600/587; 600/407
(58) Field of Classification Search ........................ None
See application file for complete search history.

(56) References Cited

U.S. PATENT DOCUMENTS

| 4,459,990 A | 7/1984 | Barnea ........................ 128/656 |
| 4,969,200 A | 11/1990 | Manns et al. ................... 382/8 |
| 4,995,068 A | 2/1991 | Chou et al. .................. 378/189 |
| 5,278,915 A | 1/1994 | Chupeau et al. ................. 382/1 |
| 5,295,200 A | 3/1994 | Boyer ........................... 382/43 |
| 5,315,630 A | 5/1994 | Sturm et al. ................... 378/65 |
| 5,434,903 A | 7/1995 | Hoornaert et al. ............ 378/116 |
| 5,447,154 A | 9/1995 | Cinquin et al. ............ 128/653.1 |
| 5,538,494 A | 7/1996 | Matsuda |
| 5,740,225 A | 4/1998 | Nabatame ..................... 378/65 |

FOREIGN PATENT DOCUMENTS

FI 79458 9/1989

OTHER PUBLICATIONS

Seppo Peltola, Gated Radiotherpapy to Compensate for Patient Breathing, May 1986.
G. Baroni, G. Ferrigno, A. Pedotti, Technology and Health Care 3 (1996) 251–262, Optoelectronic techniques for patient repositioning in radiotherapy.
Ahlstrom et al., "Pulmonary MR Angiography with Ultrasmall Superparamagnetic Iron Oxide Particles as a Blood Pool Agent and a Navigator Echo for Respiratory Gating: Pilot Study," Radiology, vol. 211, No. 3, pp. 865–869, Jun. 1999.
Antonuk et al., "A High–Resolution, High Frame Rate, Flat–Panel TFT Array for Digital X–Ray Imaging," Proceedings of SPIE, vol. 2163. pp. 118–128, 1994.
Axel et al., "Respiratory Effects in Two–Dimensional Fourier Transform MR Imaging," Radiology, vol. 160, No. 3, pp. 795–801, Sep. 1986.

(Continued)

*Primary Examiner*—Jeanne M Clark

(57) ABSTRACT

A camera generates digital image signals representing an image of one or more natural or artificial fiducials on a patient positioned on treatment or diagnosis equipment. A processor applies multiple levels of filtering at multiple levels of resolution to repetitively determine successive fiducial positions. A warning signal is generated if movement exceeds certain limits but is still acceptable for treatment. Unacceptable displacement results in termination of the treatment beam. Tracking templates can be generated interactively from a display of the digital image signals or through automatic selection of an image having the median correlation to an initial template. A gating signal synchronized to patient breathing can be extracted from the digital image signals for controlling the radiation beam generator.

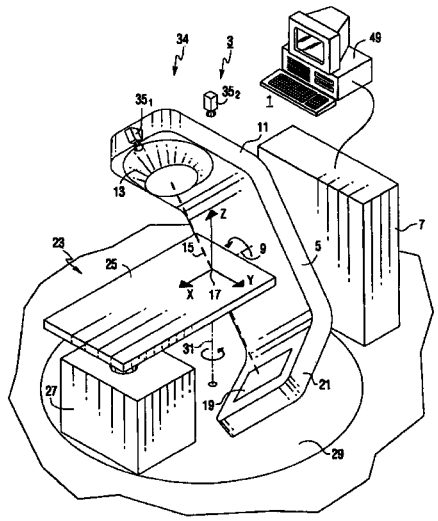

OTHER PUBLICATIONS

Baily et al., "Fluoroscopic Visualization of Megavoltage Therapeutic X Ray Beams," Int. J. Radiation Oncology Biol. Phys., vol. 6, pp. 935–939, 1980.

Ballard et al., "Computer Vision," Prentice Hall, pp. 65–72, 102–113, and 199–207, 1982.

Balter et al., "Correlation of Projection Radiographs in Radiation Therapy Using Open Curve Segments and Points" Am. Assoc. Phys. Med. 19 (2), pp. 329–334, 1992.

Balter et al., "Uncertainties in CT–Based Radiation Therapy Treatment Planning Associated with Patient Breathing," Int. J. Radiation Oncology Biol. Phys., vol. 36, No. 1, pp. 167–174, 1996.

Baroni et al., "Real–Time Motion Analysis for Definition and Control of Patient Position in Radiotherapy," SPIE vol. 2709, pp. 506–515, 1996.

Behbehani et al., "A Microprocessor–Based Sleep Apnea Ventilator," IEEE Engineering in Medicine and Biology, 11th Annual International Conference, pp. 332–333, 1989.

Bel et al., "A Verification Procedure to Improve Patient Set–Up Accuracy Using Portal Images," Radiotherapy and Oncology 29, pp. 253–260, 1993.

Bijhold et al., "Automatic Verification of Radiation Field Shape Using Digital Portal Images," Am. Assoc. Phys. Med. 19 (4), pp. 1007–1014, 1992.

Bijhold et al., "Fast Evaluation of Patient Set–Up During Radiotherapy by Aligning Features in Portal and Simulator Images," Phys. Med. Biol., vol. 36, No. 12, pp. 1665–1679, 1991.

Bijhold et al., "Radiation Field Edge Detection in Portal Images," Phys. Med. Biol., vol. 36, No. 12, pp. 1705–1710, 1991.

Bijhold, J., "Three–Dimensional Verification of Patient Placement During Radiotherapy Using Portal Images," Am. Assoc. Phys. Med. 20 (2), pp. 347–356, 1993.

Bissett et al., "Quantitative VS. Subjective Portal Verification Using Digital Portal Images," Int. J. Radiation Oncology Biol. Phys., vol. 34, No. 2, pp. 489–495, 1996.

Bissett et al., "Radiotherapy Portal Verification: An Observer Study," The British Journal of Radiology, 68, pp. 165–174, 1995.

Black et al., "A Framework for the Robust Estimation of Optical Flow," IEEE, pp. 231–236, Nov. 5, 1993.

Black et al., "Tracking and Recognizing Facial Expression in Image Sequences, Using Local Parameterized Models of Image Motion," DACAC76–92, 42 pages, Jan. 1995.

Bohning et al., "PC–Based System for Retrospective Cardiac and Respiratory Gating of NMR Data," Magnetic Resonance in Medicine, vol. 16, pp. 303–316, 1990.

Boyer et al., "A Portal Image Correlation Procedure," Medical Physics, vol. 19, No. 3, p. 802, May/Jun. 1992 (Abstract).

Boyer, A., "Present and Future Developments in Radiotherapy Treatment Units," Seminars in Radiation Oncology, vol. 5, No. 2, pp. 146–155, Apr. 1995.

Crooks et al., "Contrast Enhancement of Portal Images by Selective Histogram Equalization," Am. Assoc. Phys. Med. 20 (1), pp. 199–204, 1993.

Davatzikos et al., "Image Registration Based on Boundary Mapping," IEEE Transactions on Medical Imaging, vol. 15, No. 1, pp. 112–115, Feb. 1996.

Debois et al., "Verification of Lung Position and Inflation for Breath Hold Treatment of Lung Tumors Using On–Line Imaging," Med. Phys. vol. 23, No. 6, pp. 1082–1083, Jun. 1996.

De Neve et al., "Interactive Use of On–Line Portal Imaging in Pelvic Radiation," Int. J. Radiation Oncology Biol. Phys., vol. 25, pp. 517–524, 1993.

De Neve et al., "Routine Clinical On–Line Portal Imaging Followed by Immediate Field Adjustment Using a Tele–Controlled Patient Couch," Radiotherapy and Oncology, 24, pp. 45–54, 1992.

Dong et al., "An Image Correlation Procedure for Digitally Reconstructed Radiographs and Electronic Portal Images," Int. J. Radiation Oncology Biol. Phys., vol. 33, No. 5, pp. 1053–1060, 1995.

Dong et al., An Objective Method for Evaluating Electronic Portal Imaging Devices, Am. Assoc. Phys. Med. 21 (6), pp. 755–760, 1994.

Ehman et al., "Magnetic Resonance Imaging with Respiratory Gating: Techniques and Advantages," AJR, vol. 43, pp. 1175–1182, Dec. 1984.

Eilertsen et al., "Methods for Fully Automated Verification of Patient Set–Up in External Beam Radiotherapy with Polygon Shaped Fields," Phys. Med. Biol. 39, pp. 993–1012, 1994.

Essers et al., "Transmission Dosimetry with a Liquid–Filled Electronic Portal Imaging Device," Int. J. Radiation Oncology Biol. Phys., vol. 34, No. 4, pp. 931–941, 1996.

Evans et al., "Image Comparison Techniques for Use with Megavoltage Imaging Systems," The British Journal of Radiology, 65, pp. 701–709, 1992.

Ferrigno et al., "Three–Dimensional Optical Analysis of Chest Wall Motion," J. Appl. Physiology, vol. 77, Issue 3, pp. 1224–1231, 1994.

Fritsch et al., "Core–Based Portal Image Registration for Automatic Radiotherapy Treatment Verification," Int. J. Radiation Oncology Biol. Phys., vol. 33, No. 5, pp. 1287–1300, 1995.

Fritsch et al., "Cores for Image Registration," Proc. SPIE Med. Imaging '94, Image Processing, pp. 1–15, 1994.

Gall et al., "A System for Diagnostic Quality Radiographic Alignment of Radiotherapy Patients," Int. J. Radiation Oncology • Biology • Physics, vol. 36, No. 1, Supplement, p. 206, 1996.

Gerig et al., "The Development and Clinical Application of a Patient Position Monitoring System," Int. J. Radiation Oncology Biol. Phys., vol. 27, Supp. 1, p. 163, 1993.

Gerig et al., "The Development and Clinical Application of a Patient Position Monitoring System," Proc. of SPIE, Videometrics III, vol. 2350, pp. 59–72, Oct. 6, 1994.

Gildersleve et al., "A Randomised Trial of Patient Repositioning During Radiotherapy Using a Megavoltage Imaging System," Radiotherapy and Oncology 31, pp. 161–168, 1994.

Gildersleve et al., "Reproducibility of Patient Positioning During Routine Radiotherapy, as Assessed by an Integrated Megavoltage Imaging System," Radiotherapy and Oncology 35, pp. 151–160, 1995.

Gilhuijs et al., "An Algorithm for Automatic Analysis of Portal Images: Clinical Evaluation for Prostate Treatments," Radiotherapy and Oncology 29, pp. 261–268, 1993.

Gilhuijs et al., "Automatic On–Line Inspection of Patient Setup in Radiation Therapy Using Digital Portal Images," Am. Assoc. Phys. Med 20 (3), pp. 667–677, May/Jun. 1993.

Gilhuijs et al., "Automatic On–line Patient Setup Analysis in Portal Images," 6th International Conference Image Analysis and Processing (Como, Italy), pp. 629–636, 1991.

Gilhuijs et al., "Automatic Three–Dimensional Inspection of Patient Setup in Radiation Therapy Using Portal Images, Simulator Images, and Computed Tomography Data," Med. Phys. 23 (3), pp. 389–399, Mar. 1996.

Gilhuijs et al., "Interactive Three Dimensional Inspection of Patient Setup in Radiation Therapy Using Digital Portal Images and Computed Tomography Data," Int. J. Radiation Oncology Biol. Phys., vol. 34, No. 4, pp. 873–885, 1996.

Gilhuijs et al., "Optimization of Automatic Portal Image Analysis," Am. Assoc. Phys. Med 22 (7), pp. 1089–1099, Jul. 1995.

Goshtasby, A., "Image Registration by Local Approximation Methods," Image and Vision Computing, vol. 6, No. 4, pp. 255–261, Nov. 1988.

Goshtasby, A., "Template Matching in Rotated Images," IEEE Transactions on Pattern Analysis and Machine Intelligence, vol. PAMI–7, No. 3, May 1985.

Graham et al., A Method to Analyze 2–Dimensional Daily Radiotherapy Portal Images from An On–Line Fiber–Optic Imaging System, Int. J. Radiation Oncology Biol. Phys., vol. 20, pp. 613–619, 1991.

Graham et al., "Preliminary Results of a Prospective Trial Using Three Dimensional Radiotherapy for Lung Cancer," Int. J. Radiation Oncology Biol. Phys., vol. 33, No. 5, pp. 993–1000, 1995.

Halverson et al., "Study of Treatment Variation in the Radiotherapy of Head and Neck Tumors Using a Fiber Optic On–Line Radiotherapy Imaging System," Int. J. Radiation Oncology Biol. Phys., vol. 21, pp. 1327–1336, 1991.

Hartford et al., "Conformal Irradiation of the Prostate: Estimating Long–Term Rectal Bleeding Risk Using Dose–Volume Histograms," Int. J. Radiation Oncology Biol. Phys., vol. 36, No. 3, pp. 721–730, 1996.

Herbin et al., "Automated Registration of Dissimilar Images: Application to Medical Imagery," Computer Vision, Graphics, and Image Processing 47, pp. 77–88, 1989.

Herman et al., "Clinical Use of On–Line Portal Imaging for Daily Patient Treatment Verification," Int. J. Radiation Oncology Biol. Phys., vol. 28, No. 4, pp. 1017–1023, 1994.

Hill et al., "Accurate Frameless Registration of MR and Ct Images of the Head: Application in Planning Surgery and Radiation Therapy," Radiology, vol. 191, No. 2, pp. 447–454, May 1994.

Humm et al., "Collision Detection and Avoidance During Treatment Planning," Int. J. Radiation Biol. Phys. vol. 33, No. 5, pp. 1101–1108, 1995.

Johnson et al., "Initial Clinical Experience with an Interactive, Video Based Patient–Positioning System for Head and Neck Treatment," Int. J. Radiation Oncology Biol. Phys., vol. 36, No. 1, Supplement, p. 204, 1996.

Jones et al., "Investigation of an FFT–Based Correlation Technique for Verification of Radiation Treatment Setup," Am. Assoc. Phys. Med. 18 (6) pp. 1116–1125, Nov./Dec. 1991.

Kalend et al., "An Artificial Computer Vision (AV) System Responsive to Patient Motions with Feedback for Computer Controlled Radiation Therapy," 6 pages.

Kessler et al., "A Graphical Simulator for Design and Verification of Computer–Controlled Treatment Delivery," Proceedings of the XIth International Conference on the use of Computers in Radiation Therapy, pp. 80–81, 1994.

Kessler et al., "Integration of Multimodality Imaging Data for Radiotherapy Treatment Planning," Int. J. Radiation Oncology Biol. Phys., vol. 21, pp. 1653–1667, 1991.

Kikinis, R., "3–D Imaging: Enhanced Reality," Medical Physics, vol. 23, No. 6, Jun. 1996.

Kim et al., "Effects of Spontaneous Respiration on Right and Left Ventricular Function: Evaluation by Respiratory and ECG Gated Radionuclide Ventriculography," J. Nucl. Med., vol. 38, pp. 173–177, 1987.

King et al., "High–Dose, Hyperfractionated, Accelerated Radiotherapy Using A Concurrent Boost for the Treatment of Nonsmall Cell Lung Cancer: Unusual Toxicity and Promising Early Results," Int. J. Radiation Oncology Biol. Phys., vol. 36, No. 3, pp. 593–599, 1996.

Komaki et al., "Apoptosis and Mitosis as Prognostic Factors in Pathologically Staged N1 Nonsmall Cell Lung Cancer," Int. J. Radiation Oncology Biol. Phys., vol. 36, No. 3, pp. 601–605, 1996.

Kubo, D., "Are Respiration Gated Treatment Feasible?" Medical Physics, vol. 23, No. 6, p. 1148, Jun. 1996.

Kubo et al., "Respiration Gated Radiotherapy Treatment: A Technical Study," Phys. Med. Biol. 41, pp. 83–91, 1996.

Kupelian et al., "Prognostic Factors in the Treatment of Node–Negative Nonsmall Cell Lung Carcinoma with Radiotherapy Alone," Int. J. Radiation Oncology Biol. Phys., vol. 36, No. 3, pp. 607–613, 1996.

Lam et al., "On–Line Portal Imaging: Computer–Assisted Error Measurement," Radiology, vol. 179, No. 3, pp. 781–873, Jun. 1991.

Lebesque et al., "Detection of Systematic Patient Setup Errors by Portal Film Analysis," Radiotherapy and Oncology, 23, p. 198, 1992.

Leszczynski et al., "A Comparative Study of Methods for the Registration of Pairs of Radiation Fields," Phys. Med Biol., 38, pp. 1493–1502, 1993.

Leszczynski et al., "A Polygon Matching Algorithm and Its Applications to Verification of Radiation Field Placement in Radiotherapy," International Journal of Bio–Medical Computing 40, pp. 59–67, 1995.

Leszczynski et al., "A Study on the Efficacy of Digital Enhancement of On–Line Portal Images," Am. Assoc. Phys. Med. 19 (4), pp. 999–1005, Jul./Aug. 1992.

Leszczynski et al., "The Application of Three Registration Techniques to Clinical On–Line Portal Images," 7 pages.

Leszczynski et al., "Verification of Radiotherapy Treatments: Computerized Analysis of the Size and Shape of Radiation Fields," Am. Assoc. Phys. Med. 20, (3), pp. 687–694, May/Jun. 1993.

Lewis et al., "Comparison of Respiratory Triggering and Gating Techniques for the Removal of Respiratory Artifacts in MR Imaging," Radiology, vol. 160, pp. 803–810, 1986.

Li et al., "Coronary Arteries: Three–Dimensional MR Imaging with Retrospective Respiratory Gating," Radiology, vol. 201, No. 3, Dec. 1996.

Lichter et al., "Recent Advances in Radiation Oncology," New England Journal of Medicine, vol. 332, No. 6, pp. 371–379, Feb. 9, 1995.

Lipcamon et al., "MRI of the Upper Abdomen Using Motion Artifact Suppression Technique (MAST)," Radiologic Technology, Vo. 59, No. 5, pp. 415–418, May/Jun. 1988.

Lopez et al., "An Artificial Neural Network Based Snore Detector," Annual International Conference of the IEEE Engineering in Medicine and Biology—Proceedings, vol. 16, p. 1107–1108, 1994.

Matthews et al., "Real–Time 3D Dose Calculation and Display: A Tool for Plan Optimization," Int. J. Radiation Oncology Biol. Phys., vol. 36, No. 1, pp. 159–165, 1996.

McKibben et al., "A Piezoelectric Respiratory Monitor for in Vivo NMR," Magnetic Resonance in Medicine, vol. 37, pp. 338–342, 1992.

McParland et al., "Digital Portal Image Registration by Sequential Anatomical Matchpoint and Image Correlations for Real–Time Continuous Field Alignment Verification," Med. Phys. 22 (7), pp. 1063–1075, Jul. 1995.

McParland, B., "Uncertainty Analysis of Field Placement Error Measurements Using Digital Portal and Simulation Image Correlations," Med. Phys. 20 (3), pp. 679–685, 1993.

Meertens et al., "A Method for the Measurement of Field Placement Errors in Digital Portal Images," Phys. Med. Biol., vol. 35, No. 3, pp. 299–323, 1990.

Michalski et al., "Prospective Clinical Evaluation of an Electronic Portal Imaging Device," Int. J. Radiation Oncology Biol. Phys., vol. 34, No. 4, pp. 943–951, 1996.

Milliken et al., "Performance Characteristics of a Video–Image–Subtraction–Based Patient Positioning System," Int. J. Radiation Oncology Biol. Phys., vol. 36, Issue 1, Supplement, p. 203, 1996 (Abstract).

Mitchie et al., "Computation and Analysis of Image Motion: A Synopsis of Current Problems and Methods," International Journal of Computer Vision, 19 (1), pp. 29–55, 1996.

Mori et al., "Accurate Contiguous Sections without Breath–Holding on Chest CT: Value of Respiratory Gating and Ultrafast CT," AJR:162, pp. 10571062, May 1994.

Moseley et al., "A Semiautomatic Method for Registration of Portal Images," Med. Phys. 21 (4), pp. 551–558, Apr. 1994.

Mubata et al., "Portal Imaging Protocol for Radical Dose Escalated Radiotherapy Treatment of Prostate Cancer," Int. J. Radiation Oncology Bio. Phys., vol. 36, No. 1, Supplement, p. 205, 1996 (Abstract).

Munro et al., "A Digital Fluoroscopic Imaging Device for Radiotherapy Localization," Int. J. Radiation Oncology Biol. Phys., vol. 18, pp. 641–649, 1990.

Munro, P., "Portal Imaging Technology: Past, Present, and Future," Seminars in Radiation Oncology, vol. 5, No. 2, pp. 115–133, Apr. 1995.

Nie et al., "Development of a Computerized Portal Verification Scheme for Pelvic Treatment Fields," Int. J. Radiation Oncology Biol. Phys., vol. 36, No. 1, Supplement, p. 205, 1996 (Abstract).

Ohara et al., "Irradiation Synchronized with Respiration Gate," Int. J. Radiation Oncology Biol. Phys., vol. 17, pp. 853–857, 1989.

O'Malley et al., "Kinematic Analysis of Human Walking Gait Using Digital Image Processing," Med. & Biol. Eng. & Computing, vol. 31, pp. 392–398, 1993.

Pisanaky et al., "Correlation of Pretherapy Prostate Cancer Characteristics with Seminal Vesicle Invasion in Radical Prostatectomy Specimens," Int. J. Radiation Oncology Biol. Phys., vol. 36, No. 3, pp. 585–591, 1996.

Post et al., "Three–Dimensional Respiratory–Gated MR Angiography of Coronary Arteries: Comparison with Conventional Coronary Angiography," AJR: 166, 1399–1404, Jun. 1996.

Radcliffe et al., "Pseudocorrelation: A Fast, Robust, Absolute Grey–Level Image Alignment," Med. Phys. 21 (6), pp. 761–769, Jun. 1994.

Richardson, R., "A Low–Cost Simulator for Testing the Respiratory Gating Function of the Brattle Physiological Synchronizer," J. Nucl. Med., vol. 21, pp. 574–575, 1980.

Ritchie et al., "Predictive Respiratory Gating: A New Method to Reduce Motion Artifacts on CT Scans," Radiology, vol. 190, pp. 847–852, 1994.

Rudat et al., "Combined Error of Patient Positioning Variability and Prostate Motion Uncertainty in 3D Conformal Radiotherapy of Localized Prostate Cancer," Int. J. Radiation Oncology Biol. Phys., vol. 35, No. 5, pp. 1027–1034, 1996.

Runge et al., "Respiratory Gating in Magnetic Resonance Imaging at 0.5 Tesla," Radiology 151: 521–523, 1984.

Saw et al., "Dose Volume Assessment of High Dose Rate $^{192}$IR Endobronchial Implants," Int. J. Radiation Oncology Biol. Phys., vol. 34, No. 4, pp. 917–922, 1996.

Shalev et al., "Video Techniques for On–Line Portal Imaging," Computerized Medical Imaging and Graphics, vol. 13, No. 3, pp. 217–226, 1989.

Sherouse et al., "Computation of Digitally Reconstructed Radiographs for Use in Radiotherapy Treatment Design," Int. J. Radiation Oncology Biol. Phys., vol. 18, pp. 651–658, 1990.

Sibley et al., "The Treatment of Stage III Nonsmall Cell Lung Cancer Using High Dose Conformal Radiotherapy," Int. J. Radiation Oncology Biol. Phys., vol. 33, No. 5, pp. 1001–1007, 1995.

Swarnakar et al., "Accurate Patient Repositioning for Fractionated Radiosurgery," Int. J. Radiation Oncology Biol. Phys., vol. 36, Issue 1, Supplement, 1996, (Abstract).

Szeliski et al., "Spline–Based Image Registration," International Journal of Computer Vision 22 (3), pp. 199–218, 1997.

Uenohara et al., "Vision–Based Object Registration for Real–Time Image Overlay," Comput. Biol. Med., vol. 25, No. 2, pp. 249–260, 1995.

van den Elsen et al., "Medical Image Matching—A Review with Classification," IEEE Engineering in Medicine and Biology, pp. 26–39, Mar. 1993.

Van den Heuvel et al., "Clinical Implementation of an Objective Computer–Aided Protocol for Intervention in Intra–Treatment Correction Using Electronic Portal Imaging," Radiotherapy and Oncology, vol. 35, pp. 232–239, 1995.

van Geuns, et al., "Magnetic Resonance Imaging of the Coronary Arteries: Clinical Results from Three Dimensional Evaluation of a Respiratory Gated Technique," Heart 82, pp. 515–519, 1999.

van Herk et al., "A Comprehensive System for the Analysis of Portal Images," Radiotherapy and Oncology 29, pp. 221–229, 1993.

van Herk et al., "A Matrix Ionisation Chamber Imaging Device for On–Line Patient Setup Verification During Radiotherapy," Radiotherapy and Oncology, 11, pp. 369–378, 1988.

van Herk et al., "Automatic Three–Dimensional Correlation of CT–CT, CT–MRI, and CT–SPECT Using Chamfer Matching," Med. Phys. 21 (7), pp. 1163–1178, 1994.

van Herk, M., "Development and Clinical Application of Three–Dimensional Image Correlation Algorithms with Emphasis on Application in Radiotherapy," Cancer Treatment Radiotherapy, p. 201, 1994, (Abstract).

Vannier, M., "Respiratory Gating by Impedance Plethysmography," The Journal of Nuclear Medicine, vol. 25, No. 10, pp. 1142–1143, 1984.

Wang et al., "A Robust Morphological Algorithm for Automatic Radiation Field Extraction and Correlation of Portal Images," Med. Phys. 21 (2), pp. 237–244, Feb. 1994.

Wang et al., "Navigator–Echo–Based Real–Time Respiratory Gating and Triggering for Reduction of Respiration Effects in Three–Dimensional Coronary MR Angiography," Radiology 198, pp. 55–60, 1996.

Weber et al., "Correlative Image Registration," Seminars in Nuclear Medicine, vol. XXIV, No. 4, pp. 311–323, Oct. 1994.

Weinhous, M., "Treatment Verification Using a Computer Workstation," Int. J. Radiation Oncology Biol. Phys., vol. 19, pp. 1549–1554, 1990.

Wells et al., "Multi–Modal Volume Registration by Maximization of Mutual Information," Medical Image Analysis, vol. 1, No. 1, pp. 35–51, 1996.

Westbrook et al., "Quality Assurance in Daily Treatment Procedure: Patient Movement During Tangential Fields Treatment," Radiotherapy and Oncology, 22, pp. 299–303, 1991.

Willoughby et al., "Evaluation and Scoring of Radiotherapy Treatment Plans Using an Artificial Neural Network," Int. J. Radiation Oncology Biol. Phys., vol. 34, No. 4, pp. 923–930, 1996.

Wong et al., "On–Line Radiotherapy Imaging with an Array of Fiber–Optic Image Reducers," Int. J. Radiation Oncology Biol. Phys., vol. 18, pp. 1477–1484, 1990.

Wong et al., "The Cumulative Verification Image Analysis Tool for Offline Evaluation of Portal Images," Int. J. Radiation Oncology Biol. Phys., vol. 33, No. 5, pp. 1301–1310, 1995.

Wood et al., "Suppression of Respiratory Motion Artifacts in Magnetic Resonance Imaging," Med. Phys. 13 (6), pp. 794–805, Nov./Dec. 1986.

Yan et al., "A New Model for 'Accept or Reject' Strategies in Off–Line and On–Line Megavoltage Treatment Evaluation," Int. J. Radiation Oncology Biol. Phys., vol. 31, No. 4, pp. 943–952, 1995.

Yan et al., "The Use of Adaptive Radiation Therapy to Reduce Setup Error: A Prospective Clinical Study," Int. J. Radiation Oncology Biol. Phys., vol. 36, No. 1, Supplement, p. 204, 1996, (Abstract).

Young et al., "Neural Network Object Recognition for Inspection of Patient Setup in Radiation Therapy Using Portal Images," Acoustics, Speech, and Signal Processing, vol. 6, pp. 3418–3421, May 1996.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 20-22 is confirmed.

New claims 23-38 are added and determined to be patentable.

Claims 1-19 were not reexamined.

23. *The apparatus of claim 21, wherein said at least one fiducial is configured to be attached to a base.*

24. *The apparatus of claim 23, wherein the base is configured to be secured to the patient's skin.*

25. *The apparatus of claim 21, wherein said image of at least one fiducial on said patient comprises an image of a fiducial placed on said patient.*

26. *The apparatus of claim 21, wherein said image of at least one fiducial on said patient comprises an image of a passive fiducial on said patient.*

27. *The apparatus of claim 21, wherein said processing means further comprises means identifying locations of said at least one fiducial using templates to indicate a patttern of digital image signals representing said image of at least one fiducial.*

28. *The apparatus of claim 21, wherein said processing means further comprises means continuously tracking said at least one fiducial.*

29. *The apparatus of claim 21, wherein said processing means further comprises software to estimate a direction and distance traveled by said at least one fiducial.*

30. *The apparatus of claim 21, wherein said processing means further comprises software to predict quasi-periodic motion associated with said at least one fiducial.*

31. *The apparatus of claim 20, wherein said camera means generates said digital image signals representing an image of a plurality of fiducials on said patient, and said means determining movement of said patient comprises means determining movement of said plurality of fiducials.*

32. *The apparatus of claim 20, wherein said processing means further comprises means generating a visible warning if the determined movement of said patient exceeds a certain tolerance.*

33. *The apparatus of claim 20, wherein said processing means further comprises means generating an audio warning if the determined movement of said patient exceeds a certain tolerance.*

34. *The apparatus of claim 20, wherein said processing means further comprises means generating a visible warning and an audio warning if the determined movement of said patient exceeds a certain tolerance.*

35. *The apparatus of claim 20, wherein said processing means further comprises means generating a color coded display to indicate a state of motion of a fiducial.*

36. *The apparatus of claim 20, wherein said processing means further comprises means displaying a green section when the determined movement is within a specified range.*

37. *The apparatus of claim 20, wherein said processing means further comprises means displaying a red section when the determined movement is outside of an acceptable range.*

38. *The apparatus of claim 20, further comprising a beam generator configured to provide computer-controlled multi-beam conformal dynamic radio therapy for said patient, wherein said gating signals are synchronized to actuate said beam generator in synchronism with patient breathing.*

\* \* \* \* \*